United States Patent
Volpert et al.

(10) Patent No.: US 10,407,633 B2
(45) Date of Patent: Sep. 10, 2019

(54) USE OF A FUEL ADDITIVE IN DIESEL FUEL FOR REMOVING DEPOSITS IN A DIESEL ENGINE

(71) Applicant: UNITED INITIATORS GMBH, Pullach (DE)

(72) Inventors: Edgar Volpert, München (DE); William A. Batson, The Woodlands, TX (US)

(*) Notice: Subject to any disclaimer, the term of this patent is extended or adjusted under 35 U.S.C. 154(b) by 0 days.

(21) Appl. No.: 15/569,411

(22) PCT Filed: Apr. 28, 2016

(86) PCT No.: PCT/EP2016/059567
§ 371 (c)(1),
(2) Date: Oct. 26, 2017

(87) PCT Pub. No.: WO2016/174178
PCT Pub. Date: Nov. 3, 2016

(65) Prior Publication Data
US 2018/0079980 A1    Mar. 22, 2018

(30) Foreign Application Priority Data
Apr. 28, 2015 (EP) .................... 15165435

(51) Int. Cl.
*C10L 1/18* (2006.01)
*C10L 1/182* (2006.01)
(Continued)

(52) U.S. Cl.
CPC .......... *C10L 1/1811* (2013.01); *C07C 409/02* (2013.01); *C07C 409/16* (2013.01); *C10L 1/026* (2013.01); *C10L 1/1616* (2013.01); *C10L 1/1824* (2013.01); *C10L 10/04* (2013.01); *C10L 10/06* (2013.01); *C10L 10/12* (2013.01); *C10L 1/1608* (2013.01); *C10L 1/191* (2013.01); *C10L 1/231* (2013.01); *C10L 10/08* (2013.01);
(Continued)

(58) Field of Classification Search
CPC combination set(s) only.
See application file for complete search history.

(56) References Cited

U.S. PATENT DOCUMENTS 2,226,543 A * 12/1940 Ashburn .................. C10M 1/08
  508/441
2,935,476 A   5/1960 Stuart et al.
(Continued)

FOREIGN PATENT DOCUMENTS

| CN | 102876425 | 1/2013 |
| CN | 103725336 | 4/2014 |

(Continued)

OTHER PUBLICATIONS

European Patent Application No. 15165435.7, extended European Search Report dated Oct. 19, 2015.
(Continued)

*Primary Examiner* — Ellen M McAvoy
*Assistant Examiner* — Chantel L Graham
(74) *Attorney, Agent, or Firm* — Kilpatrick Townsend & Stockton LLP

(57) ABSTRACT

The present invention relates to the use of a diesel fuel additive for removing deposits in a diesel engine.

25 Claims, 2 Drawing Sheets

Figure 1:
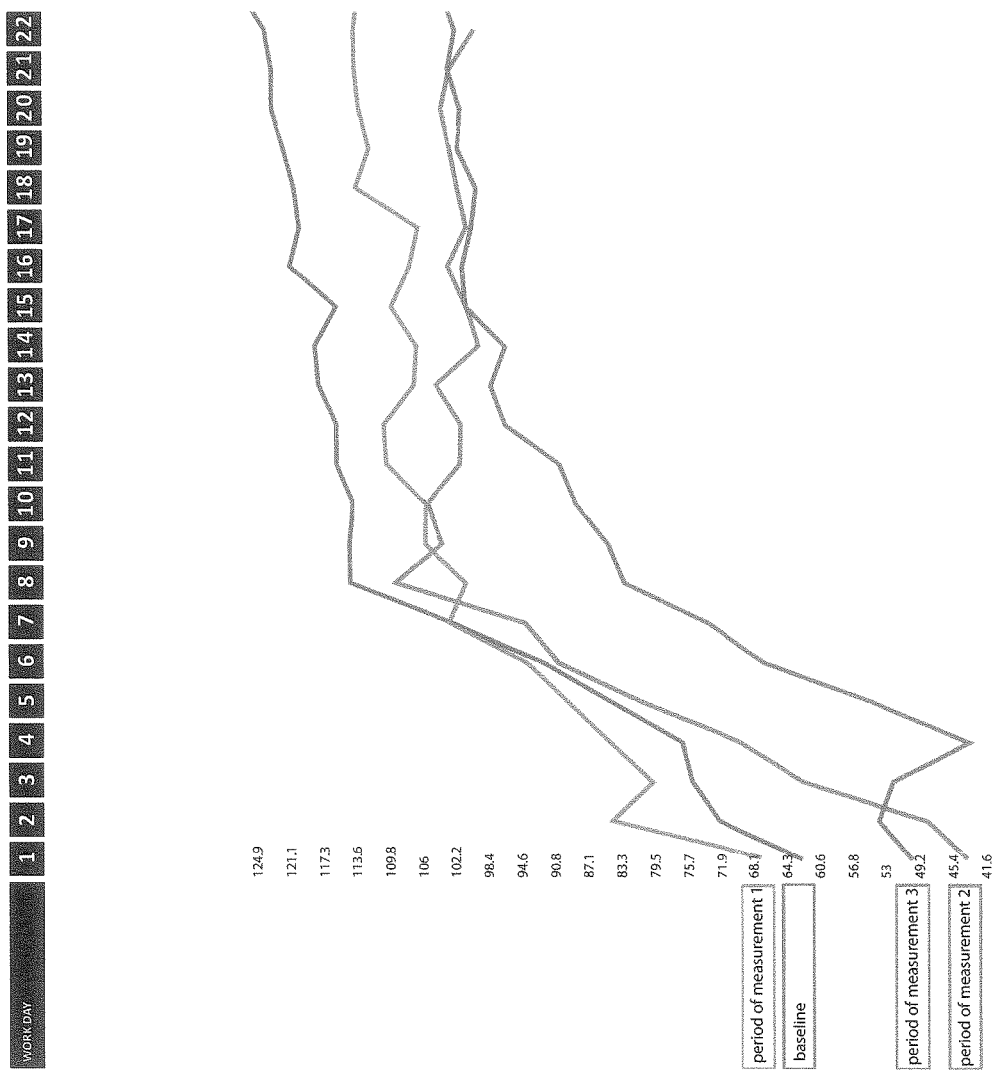

(51) Int. Cl.
*C10L 1/16* (2006.01)
*C10L 10/12* (2006.01)
*C10L 10/06* (2006.01)
*C07C 409/02* (2006.01)
*C07C 409/16* (2006.01)
*C10L 1/02* (2006.01)
*C10L 10/04* (2006.01)
*C10L 1/19* (2006.01)
*C10L 1/23* (2006.01)
*C10L 10/08* (2006.01)

(52) U.S. Cl.
CPC . *C10L 2200/043* (2013.01); *C10L 2200/0446* (2013.01); *C10L 2230/22* (2013.01); *C10L 2270/026* (2013.01)

(56) References Cited

U.S. PATENT DOCUMENTS

| | | |
|---|---|---|
| 5,314,511 A | 5/1994 | Liotta, Jr. et al. |
| 6,858,047 B1 | 2/2005 | Norman et al. |
| 2002/0026744 A1 | 3/2002 | Golubkov et al. |
| 2006/0130394 A1* | 6/2006 | Selvidge .................. C10L 1/143 44/326 |
| 2014/0150333 A1 | 6/2014 | Brewer et al. |
| 2014/0311019 A1* | 10/2014 | Gutewort .................. C10L 1/14 44/322 |

FOREIGN PATENT DOCUMENTS

| | | |
|---|---|---|
| EP | 303862 | 2/1989 |
| WO | 9932584 | 7/1999 |
| WO | 2013072478 | 5/2013 |

OTHER PUBLICATIONS

International Application No. PCT/EP2016/059564, International Search Report and Written Opinion, dated Jun. 30, 2016.
International Application No. PCT/EP2016/059564, International Preliminary Report on Patentability, dated Jul. 26, 2017.
International Application No. PCT/EP2016/059567, International Search Report and Written Opinion, dated Jun. 30, 2016.
International Application No. PCT/EP2016/059567, International Preliminary Report on Patentability, dated Jul. 26, 2017.

* cited by examiner

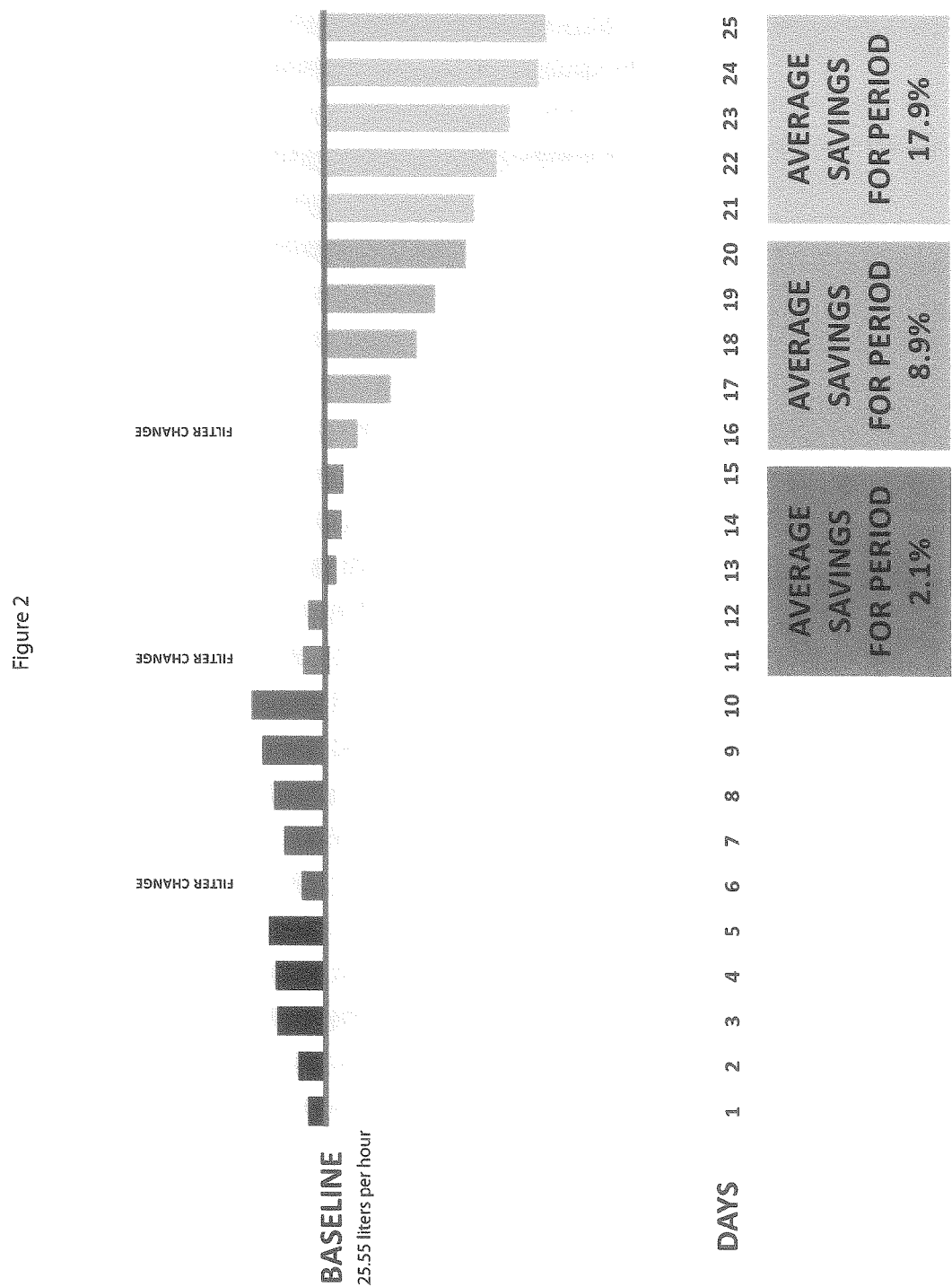

USE OF A FUEL ADDITIVE IN DIESEL FUEL FOR REMOVING DEPOSITS IN A DIESEL ENGINE

The present invention relates to the use of a diesel fuel additive for removing deposits in a diesel engine.

Undesired deposits in an engine can be formed e.g. due to incomplete combustion of the fuel, impurities in the fuel or/and suction of impurities from air. During combustion apart from volatile gases also finest solids or particles are formed. These particles can deposit inter alia on the fuel injection valves and channels and/or the combustion chamber of the engine.

Undesired deposits in an engine have a great influence on the wear, fuel consumption and economic use of an engine. Contaminants or deposits can increase the wear of an engine. This means that an engine with more deposits in an engine is subjected to greater wear compared to the same engine without or with less deposits. Contaminants or deposits in an engine can also decrease its performance. Performance can be understood as that less energy is provided by an engine with more deposits compared to the same engine without or less deposits in the engine. This can be seen inter alia in an increase of fuel consumption of an engine with deposits compared to an engine without deposits in the engine. This can have a great effect on the economic use of an engine.

It is desired to prevent, reduce and/or remove deposits to decrease wear and fuel consumption in an engine.

The published patent application EP 2 780 435 A1 describes the use of TBHP as fuel additive for reducing carbon monoxide and/or hydrocarbon emission as well as increasing the cetane number.

It was an object of the present invention to achieve prevention, reduction and/or removal of deposits in diesel engines.

This object is solved with a fuel additive for diesel fuels comprising a peroxide, particularly tert-butyl hydroperoxide (TBHP).

The invention therefore relates to the use of a fuel additive comprising a peroxide in a diesel fuel for prevention, reduction and/or removal of deposits in a diesel engine.

Surprisingly, it has been found that by using peroxides, wherein TBHP is particularly preferred, a prevention, reduction and/or removal of deposits in diesel engines is effected.

The use of a peroxide-containing fuel additive provides prevention, reduction or removal of undesired deposits or contaminants in a diesel engine. Thereby it is understood that the use of a peroxide-containing diesel additive prevents the formation of new deposits or contaminants and/or reduces and/or removes already existing deposits or contaminants in the engine.

Particular examples of deposits or contaminants comprise small particles, soot or/and glycol.

Examples 1-5 and FIGS. 1-2 of this application impressively demonstrate the results of prevention, reduction and/or removal of deposits.

A fuel additive is a composition added to a fuel, preferably in amounts of 0.001 to 50 wt. %, more preferably between 0.01 to 25 wt %, more preferably between 0.1 to 10 wt. % related to the total weight of the fuel. Even more preferably, the fuel additive is added to a fuel in an amount of 0.1 to 1 wt. % related to the total weight of the fuel. By adding a fuel additive to the fuel, the fuel additive and the fuel preferably form a solution.

The fuel additive to be used according to the invention comprises a peroxide, particularly an organic peroxide and preferably TBHP.

The fuel additive to be used according to the invention preferably does not comprise metal peroxides, in particular does not comprise barium peroxide or strontium peroxide, or a mixture thereof.

In general various organic peroxides can be used as fuel additives. A preferred embodiment is the use of a fuel additive comprising at least one hydroperoxide, dialkylperoxide, cyclic or acyclic ketone peroxide or/and perketal. Further preferred is the use of a fuel additive comprising at least one hydroperoxide, dialkylperoxide or/and a cyclic or acyclic ketone peroxide. Particularly preferred is the use of a fuel additive comprising at least one hydroperoxide and/or dialkylperoxide. Also particularly preferred is the use of a fuel additive comprising at least one perketal.

Hydroperoxides, in particular alkyl-, acyl- or/and arylhydroperoxides, have the general structural formula R—O—O—H.

Dialkylperoxides, in particular cyclic and acyclic dialkylperoxides, have the general structural formula $R^1$—O—O—$R^2$. In cyclic dialkylperoxides the residues $R^1$ and $R^2$ together form a 4 to 10 membered cycle, more preferably a 5 to 7 membered cycle.

Cyclic ketone peroxides have the general structural formula $(R^1R^2C(-O-O-))_n$, wherein n can be an integer from 2 to 6, the peroxidic bond is formed between the C-atoms to form a cycle, and $R^1$ and $R^2$ represent identical or different organic residues.

Acyclic ketone peroxides have the general structural formula $R^1R^2C(-O-O-H)-O-O-C(-O-O-H)R^3R^4$, wherein $R^1$, $R^2$, $R^3$ and $R^4$ represent identical or different organic residues.

Perketals have the general structure R—O—O—$R^1$—O—O—R, wherein R and $R^1$ represent identical or different organic residues.

The residues R, $R^1$, $R^2$, $R^3$ and $R^4$ represent each independently an organic residue, in particular a hydrocarbon residue with 1 to 3 heteroatoms.

The residues R, $R^1$, $R^2$, $R^3$ and $R^4$ represent each independently acyclic linear chain alkyl, preferably having 1 to 20, preferably 3 to 10 carbon atoms and can be unsubstituted or substituted with at least one —OMe, —OH, aryl or/and heteroaryl;

acyclic branched chain alkyl, preferably having 1 to 20, preferably 3 to 10 carbon atoms and can be unsubstituted or substituted with at least one —OMe, —OH, aryl or/and heteroaryl;

acyl, wherein acyl represents a moiety having the structural formula RC(O)—;

aryl, wherein aryl is an aromatic moiety with 6 to 10 C-atoms, which can be unsubstituted or substituted with —OMe or/and —OH;

heteroaryl, wherein heteroaryl is an aromatic moiety with 4 to 10 C-atoms comprising one or more heteroatoms, particularly nitrogen or/and oxygen in the aromatic system, and can be unsubstituted or substituted with —OMe or/and —OH; or cyclic alkyl, preferably having 3 to 10, more preferably 5 to 8 carbon atoms forming a cycle and can be unsubstituted or substituted with a least one —OMe, —OH, acyclic linear chain alkyl or/and acyclic branched chain alkyl.

In a preferred embodiment the fuel additive comprises tert-butylhydroperoxide (TBHP), cumene hydroperoxide, methylethyl ketone peroxide, in particular cyclic or acyclic methylethyl ketone peroxide, acetone peroxide, tert-amyl hydroperoxide (TAHP), di-tert-butyl peroxide (DTBP), tert-butyl peroxybenzoate (TBPB), 1,1-Di-(tert-butylperoxy)-cyclohexane (CH), tetramethyl-dioxa-cyclohexane (TM-DOCH) or 1,1-bis-(tert-butylperoxy)-3,3,5-trimethylcyclohexane (TMCH), 1,1-bis-(tert-amylperoxy)-cyclohexane, 2,2-di-(tert-butylperoxy)-butane (BH), ethyl-3,3-di-(tert-butylperoxy)-butanoate (EBU) or 4,4-bis-(tert-butylperoxy)-valeric acid-n-butyl ester (NBV) or mixtures thereof.

Specifically when using a fuel additive comprising hydroperoxide, dialkylperoxide or/and cyclic or acyclic ketone peroxide or/and perketal, particularly tert-butyl hydroperoxide (TBHP), cumene hydroperoxide, methylethyl ketone peroxide, in particular cyclic and/or acyclic methylethyl ketone peroxide, acetone peroxide, tert-amyl hydroperoxide (TAHP), di-tert-butyl peroxide (DTBP), tert-butyl peroxybenzoate (TBPB), 1,1-Di-(tert-butylperoxy)-cyclohexane (CH), tetramethyl-dioxa-cyclohexane (TM-DOCH), or/and 1,1-bis-(tert-butylperoxy)-3,3,5-trimethylcyclohexane (TMCH), 1,1-bis-(tert-amylperoxy)-cyclohexane, 2,2-di-(tert-butylperoxy)-butane (BH), ethyl-3,3-di-(tert-butylperoxy)-butanoate (EBU) or 4,4-bis-(tert-butylperoxy)-valeric acid-n-butyl ester (NBV) or mixtures thereof a prevention, reduction and/or removal of deposits in diesel engines has been observed.

Preferably, the fuel additive comprises TBHP, DTBP and/or CH.

Most preferably the fuel additive comprises TBHP.

Organic peroxides are thermally unstable compounds, which decompose exothermically with cleavage of the peroxidic oxygen bond. Therefore, for the safe handling or safe transport of organic peroxides they must, for safety considerations often be phlegmatised or are produced industrially already in dilution.

Commercially available peroxide preparations often contain large amounts of water as phlegmatiser, have insufficient thermal or chemical stability or cannot be used commercially as a fuel additive due to the raw materials or production processes used. Preferably, peroxides phlegmatised with water should be avoided as a fuel additive, because water does not mix with the fuel but forms a two-phase system.

Therefore, preferably an anhydrous fuel additive is used. Particularly preferred the fuel additive of the invention comprises anhydrous TBHP, DTBP and/or CH, even more preferably the fuel additive of the invention comprises anhydrous TBHP. Anhydrous means that the content of water in the fuel additive is <5 wt. %, particularly <1 wt. %, yet more preferably <0.3 wt. %, most preferably <0.01 wt. %.

By using anhydrous peroxide, which is miscible with diesel fuel, the formation of an undesirable second aqueous phase can be avoided. The fuel additive, in addition to a peroxide preferably comprises an anhydrous organic solvent. Polar and non-polar solvents can be used. Examples of suitable non-polar solvents are alkanes, in particular aliphatic hydrocarbons such as isododecane, isooctane, decane, nonane and/or n-octane or mixtures of different aliphates. A particularly suitable non-polar solvent is the aliphatic hydrocarbon isododecane. In particular, suitable examples of solvents are diesel and kerosene. Further examples of suitable hydrocarbons are cyclic and acyclic hydrocarbons with 5 to 12, preferably 6 to 10 carbons either saturated or unsaturated. Examples of polar solvents are particularly oxygen-containing solvents, such as, for example, esters and alcohols. Suitable esters used as solvents are in particular phthalates and 2,2,4-trimethyl-1,3-pentanediol diisobutyrate (TXIB). Alkyl alcohols are preferably used as solvents, particularly C1-C8 alkyl alcohols, more preferably C2-C6 alkyl alcohols, yet more preferably butanol and most preferably tert-butanol (TBA). By using alcohols and particularly tert-butanol, the oxygen content in the fuel additive is increased further, which is desirable.

Preferably, the fuel additive comprises a hydroperoxide, dialkylperoxide and/or perketal, particularly TBHP, DTBP and/or CH, and an organic solvent. More preferably, the fuel additive comprises an anhydrous hydroperoxide, an anhydrous dialkylperoxide or/and anhydrous perketal, particularly anhydrous TBHP, anhydrous DTBP or/and anhydrous CH and an organic solvent.

Particularly preferred is a fuel additive comprising TBHP and an organic solvent, particularly tert-butanol (TBA). Even more preferred is a fuel additive comprising anhydrous TBHP and an organic solvent, particularly tert-butanol (TBA).

According to the invention the additive containing peroxide is added to a diesel fuel. Diesel fuels can comprise, for example, diesel, biodiesel or marine diesel.

Preferably the diesel fuel containing the peroxide-containing diesel additive is anhydrous. Anhydrous means that the diesel fuel containing the peroxide-containing diesel additive has a total content of water of <5 wt. %, particularly <1 wt. %, more preferably <0.3 wt. %, yet more preferably <0.1 wt. %, even more preferably <0.03 wt. %, more preferably <0.01 wt. %, yet even more preferably <0.001 wt. %, most preferably <0.0001 wt. %.

Particularly good results are obtained when the additive containing peroxide is added to a fuel exhibiting a low diesel grade, such as various marine diesel or diesel as used in many non-EU countries.

Low diesel grades or diesel fuels of a low quality have a cetane number without fuel additive of <50, more preferred <45, even more preferred ≤42, yet more preferred ≤40, whereas higher diesel qualities have a cetane number ≥50, more preferred ≥51. Low grade diesel fuels have a minimum cetane number without fuel additive of >20, preferably >25, more preferably >30. The cetane number can be determined according to ASTM-D613, for example.

The cetane number is a characteristic parameter for the combustion quality of diesel fuel. The cetane number is a measure of the ease of ignition or the ignition delay, that is to say the time between the start of fuel injection and the start of combustion. Rapid ignition followed by uniform combustion is advantageous. The higher the cetane number, the shorter the ignition delay and the better the combustion quality.

Now it has been found that the use of a peroxide-containing fuel additive provides a prevention, reduction and/or removal of deposits in a diesel engine, when low grade diesel qualities such as commercially available US diesel, are applied. In this respect, peroxides are also suitable e.g. as fuel additives for prevention, reduction and/or removal of deposits in regions, where typically low grade diesel fuels are applied.

Preferably the peroxide-containing fuel additive applied according to the invention increases the cetane number of a fuel with fuel additive by at least 2, more preferred by at least 3, yet more preferred by at least 5, most preferred at least by 7 compared to the cetane number of the same fuel without fuel additive.

A diesel fuel admixed with the peroxide-containing additive can be applied in diesel engines such as used in automotives or ships or provided for stationary diesel engines to generate energy. A particular prevention, reduction and/or removal of deposits is effected in low compression diesel engines. Compared to modern diesel engines complying with current Euro 5 standard, low compression diesel engines exhibit a lower compression ratio. Modern high compression diesel engines exhibit a compression ratio of at least 19:1, more preferred at least 21:1. In contrast, low compression diesel engines exhibit a compression ratio of less than 19:1, particularly of less than 18:1 and preferably less than 16:1.

The compression ratio describes the ratio of the total cylinder chamber prior to compression to the remaining space after compression. The compression of the cylinder chamber causes a rise in temperature in the cylinder chamber. A high compression ratio provides easy self-ignition.

Further, the size of displacement per cylinder determines the quality of combustion in a diesel engine. A particular prevention, reduction and/or removal of deposits by addition of a peroxide, particularly TBHP, is discovered in engines with a large displacement per cylinder, particularly for a displacement of at least 1000 $cm^3$, more preferably at least 2000 $cm^3$, yet even more preferably at least 3000 $cm^3$ per cylinder. A large displacement per cylinder effects worse mixing or blending of the fuel with air. Thus, without additive, there is worse or incomplete combustion of the fuel.

Displacement or displaced volume describes the enclosed volume of a cylinder in a combustion engine, which results from the stroke of a single piston and the effective piston cross section. The cylinder displacement hence is the volume displaced by the stroke of the piston in a combustion engine.

The amount of peroxide, particularly TBHP, DTBP or/and CH, more particularly TBHP, in the fuel additive is preferably at least 10 wt. %, more preferably at least 30 wt. %, yet more preferably at least 40 wt. %, most preferably at least 50 wt. %. Pure peroxide is not preferred for safety considerations. However, pure peroxide may also be suitable for the use as a fuel additive according to the invention. The amount of peroxide, particularly TBHP, DTBP or/and CH, more particularly TBHP in the fuel additive is therefore preferably up to 90 wt. %, more preferably up to 75 wt % and most preferably up to 60 wt. %. The amount of anhydrous organic solvent, particularly alcohols and preferably tert-butanol (TBA), is accordingly at least 10 wt. %, more preferably at least 25 wt. % and most preferably at least 40 wt. % and up to 90 wt. %, more preferably up to 70 wt. % and most preferably up to 50 wt. %.

A fuel additive that comprises 30 to 70 wt. % peroxide in 70 to 30 wt. % alcohol has been shown to be particularly suitable and accordingly most preferred. A fuel additive that comprises 20 to 80 wt. % peroxide in 80 to 20 wt. % alcohol has also been shown to be particularly suitable and accordingly most preferred. A fuel additive that comprises 50 to 60 wt. % peroxide in 60 to 50 wt. % alcohol is yet more preferred. A fuel additive that comprises 40 to 60 wt % peroxide in 60-40 wt. % alcohol is even more preferred. A fuel additive that comprises 55 wt. % peroxide and 45 wt. % alcohol is most preferred. Due to the production process, peroxides can be phlegmatised by an oxygen-containing solvent, preferably in an alcohol, particularly in tert-butanol, thereby improving safety during transport and further handling.

A fuel additive that comprises 30 to 70 wt. % TBHP in 70 to 30 wt. % tert-butanol (TBA) has been shown to be particularly preferred. A fuel additive that comprises 50 to 60 wt. % TBHP in 60 to 50 wt. % tert-butanol is yet more preferred. A fuel additive that comprises 40 to 60 wt % TBHP in 60-40 wt % tert-butanol is even more preferred. A fuel additive that comprises 55 wt. % TBHP and 45 wt. % tert-butanol is most preferred.

It has been found that a prevention, reduction and/or removal of deposits can be achieved even with small amounts of fuel additive.

The peroxide, particularly TBHP, DTBP or/and CH, more particularly TBHP, is applied in an amount of 0.001 to 10 wt. %, more preferably from 0.01 to 8 wt. %, more preferably from 0.025 to 5 wt. %, yet more preferably from 0.055 to 4 wt. % most preferably from 0.1 to 3 wt. %, and, in particular from 0.1 to 0.5 wt. %, based on the total weight of the fuel.

In a preferred embodiment the invention relates to the use of a diesel fuel additive in a diesel fuel for preventing, reducing and/or removing deposits in a diesel engine characterized in that the fuel additive comprises an organic peroxide being applied in an amount from 0.025 to 10 wt. %, in particular from 0.1 to 3 wt. %, even more particularly from 0.1 to 0.5 wt. %, based on the total weight of the fuel.

In another preferred embodiment the invention relates to the use of a diesel fuel additive in a diesel fuel for preventing, reducing and/or removing deposits in a diesel engine characterized in that the fuel additive comprises an anhydrous organic peroxide being applied in an amount from 0.025 to 10 wt. %, in particular from 0.1 to 3 wt. %, even more particularly from 0.1 to 0.5 wt. %, based on the total weight of the fuel.

In yet another preferred embodiment the invention relates to the use of a diesel fuel additive in a diesel fuel for preventing, reducing and/or removing deposits in a diesel engine characterized in that the fuel additive comprises an anhydrous organic peroxide being applied in an amount from 0.025 to 10 wt. %, in particular from 0.1 to 3 wt. %, even more particularly from 0.1 to 0.5 wt. %, based on the total weight of the fuel and the diesel fuel has a cetane number of <45 without fuel additive.

In a particular preferred embodiment the invention relates to the use of a diesel fuel additive in a diesel fuel for preventing, reducing and/or removing deposits in a diesel engine characterized in that the fuel additive comprises anhydrous TBHP and TBA. In a further particular preferred embodiment the invention relates to the use of a diesel fuel additive in a diesel fuel for preventing, reducing and/or removing deposits in a diesel engine characterized in that the fuel additive comprises anhydrous DTBP or/and CH.

In another preferred embodiment the invention relates to the use of a diesel fuel additive in a diesel fuel for preventing, reducing and/or removing deposits in a diesel engine characterized in that the fuel additive comprises is anhydrous TBHP and TBA, wherein TBHP is applied in an amount from 0.025 to 10 wt. %, in particular from 0.1 to 3 wt. %, even more particularly from 0.1 to 0.5 wt. %, based on the total weight of the fuel.

In yet another preferred embodiment the invention relates to the use of a diesel fuel additive in a diesel fuel for preventing, reducing and/or removing deposits in a diesel engine characterized in that the fuel additive comprises anhydrous TBHP and TBA wherein TBHP is applied in an amount from 0.025 to 10 wt. %, in particular from 0.1 to 3 wt. %, even more particularly from 0.1 to 0.5 wt. %, based on the total weight of the fuel and the diesel fuel has a cetane number of <45 without fuel additive.

It is also possible according to the invention to combine the fuel additive and/or the fuel with other components. Preference is given, for example, to an additive comprising at least two peroxides, particularly selected from hydroperoxides, dialkylperoxides, cyclic or acyclic peroxides and/or perketals. Preference is further given, for example, to an additive comprising at least two peroxides, particularly selected from hydroperoxides, dialkylperoxides and/or cyclic or acyclic ketone peroxides. Particularly preferred is tert-butyl hydroperoxide (TBHP) in combination with a further peroxide, particularly selected from cumene hydroperoxide, di-tert-butylperoxide (DTBP), methylethyl ketone peroxide, in particular cyclic and/or acyclic methylethyl ketone peroxide, acetone peroxide, tert-amyl hydroperoxide (TAHP), di-tert-butyl peroxide (DTBP), tert-butyl peroxybenzoate (TBPB), 1,1-Di-(tert-butylperoxy)-cyclohexane (CH), tetramethyl-dioxa-cyclohexane (TMDOCH) or/and 1,1-bis-(tert-butylperoxy)-3,3,5-trimethylcyclohexane (TMCH), 1,1-bis-(tert-amylperoxy)-cyclohexane, 2,2-di-(tert-butylperoxy)-butane (BH), ethyl-3,3-di-(tert-butylperoxy)-butanoate (EBU) or 4,4-bis-(tert-butylperoxy)-valeric acid-n-butyl ester (NBV). Further, an additive is preferred that comprises at least one peroxide and additionally tert-butylalcohol or/and 2-ethylhexylnitrate (2-EHN).

Preferably, prevention, reduction and/or removal of deposits in an engine can be observed by continuously or constantly using the peroxide-containing fuel additive during the entire operation time.

Preferably, prevention, reduction and/or removal of deposits in an engine can be observed when the fuel containing the peroxide-containing fuel additive is used in a diesel engine for a runtime or operation time of at least 100 hrs, preferred at least 170 hrs, more preferred at least 240 hrs and most preferred at least 310 hrs.

Preferably, prevention, reduction and/or removal in the engine can be observed when the fuel containing the peroxide-containing fuel additive is continuously used in the diesel engine for a runtime or operation time of at least 4 days, preferred at least 7 days, more preferred at least 10 days and most preferred at least 13 days.

It is less preferred, although also possible, that the prevention, reduction and/or removal of deposits in the engine can be achieved by adding a fuel containing the peroxide-containing fuel additive in intervals. Thereby it is understood that the fuel with the peroxide-containing fuel additive is added in certain time intervals while using fuel without the peroxide-containing fuel additive otherwise. Preferably, the amount of added fuel with the peroxide-containing fuel additive is at least 10 liters, preferably at least 20 liters, more preferred at least 40 liters and most preferred at least 60 liters. Preferably, the fuel containing the peroxide-containing fuel additive is used for 10 to 1000 hours, preferred 50 to 500 hours, more preferred 100 to 250 hours alternating with using the fuel without the peroxide-containing fuel additive for 10 to 1000 hours, preferred 50 to 500 hours, more preferred 100 to 250 hours.

It was observed that the use of a peroxide-containing fuel additive particularly provides a reduction of diesel fuel consumption by at least 5%, more preferably by at least 7%, yet more preferably by at least 10%, even more preferably by at least 13% compared to a similar diesel fuel without fuel additive.

Preferably, reduction of fuel consumption in an engine can be observed by continuously or constantly using the peroxide-containing fuel additive during the entire operation time.

Preferably, reduction in fuel consumption can be observed when the fuel containing the peroxide-containing fuel additive is continuously used in a diesel engine for a runtime or operation time of at least 100 hours, preferred at least 170 hours, more preferred at least 240 hours and most preferred at least 310 hours.

Preferably, reduction in fuel consumption can be observed when the fuel containing the peroxide-containing fuel additive is continuously used in a diesel engine for a runtime or operation time of at least 4 days, preferred at least 7 days, more preferred at least 10 days and most preferred at least 13 days.

It is less preferred, although also possible, that the fuel consumption in an engine can be reduced by adding the fuel containing the peroxide-containing fuel additive in intervals. Thereby it is understood, that certain amounts of to fuel with the peroxide-containing fuel additive is added in certain time intervals while using fuel without the peroxide-containing fuel additive otherwise. Preferably, the amount of added fuel with the peroxide-containing fuel additive is at least 10 liters, preferably at least 20 liters, more preferred at least 40 liters and most preferred at least 60 liters. Preferably, the fuel containing the peroxide-containing fuel additive is used for 10 to 1000 hours, preferred 50 to 500 hours, more preferred 100 to 250 hours alternating with using the fuel without the peroxide-containing fuel additive for 10 to 1000 hours, preferred 50 to 500 hours, more preferred 100 to 250 hours.

Further, it was observed that the use of a peroxide-containing fuel additive provides a reduction in friction and wear of the diesel engine. Reduction in friction and wear can be achieved when a fuel additive with high lubrication is used. The HFRR (high frequency reciprocating rig) score is a characteristic parameter for the lubrication of a fuel or a fuel additive. The HFRR score can be determined according to ASTM-D6078 and ASTM-D6079, for example. A high HFRR score is determined for a fuel or fuel additive with bad lubrication as for example untreated ultra-low sulfur diesel having a HFRR score of 636. A high HFRR score results in high friction and wear by the fuel or fuel additive compared to a fuel or fuel additive with a low HFRR score. According to the Engine Manufacturers Association the HFRR score has to be desirably below 460.

Preferably, the fuel with peroxide-containing fuel additive has a HFRR score of at most 400, more preferred at most 370 and most preferred at most 330.

Preferably, the peroxide-containing fuel additive applied lowers the HFRR score of a fuel with fuel additive by at least 70, more preferably at least 140 and most preferably at least 210 compared to the same fuel without fuel additive.

Preferably, the peroxide-containing fuel additive applied lowers the HFRR score of a fuel with fuel additive by at least 30, more preferably at least 60 and most preferably at least 90 in comparison to the limit value of Engine Manufacturers Association.

Further, it was observed that the use of a peroxide-containing fuel additive provides a reduced smoke emission together with a cleaner (whiter) smoke emission compared to the emission generated when using untreated fuel. Consequently, the use of a peroxide-containing fuel additive provides a reduction of fuel particulate emission, e.g. soot contaminants.

The particulate matter (PM) mass is a characteristic parameter for regulating the emission of fuel combustion. The mass of PM is determined by well-known sampling methods based on the weight of PM collected on a sampling filter. Preferably, using a fuel with peroxide-containing fuel additive leads to a reduction of PM mass of at least 5%, more preferably of at least 10%, even more preferably of at least 15% compared to the PM mass of an untreated fuel measured under the same sampling conditions.

Also part of this invention is a method for preventing, reducing and/or removing deposits in a diesel engine wherein a fuel additive comprising a peroxide is added to the diesel fuel.

EXAMPLE 1

Reduction of Fuel Consumption with TBHP and TBA as Fuel Additive

To a conventional US base diesel fuel (cetane number=42) was added 0.25 wt. % of a fuel additive consisting of TBHP (55 wt. %) and TBA (45 wt. %). The total amount of TBHP added to the diesel fuel is 0.14 wt. %.

By addition of fuel additive to the above described diesel fuel the cetane number is increased from 42 (without fuel additive) to 48 (with fuel additive).

The test engine used was a Caterpillar D3512-C V12 diesel engine exhibiting a total displacement of 58560 cm$^3$, as well as a displacement per cylinder of 4880 cm$^3$ and a compression ratio of 14.7:1. The test engine was used in a drilling rig.

In a comparative test the consumption of the above mentioned US base diesel fuel was measured without and with diesel fuel additive consisting of TBHP and TBA in the Caterpillar D3512-C diesel engine over a continuous period of time of 22 days. The measurement of fuel consumption of the US base diesel fuel without diesel fuel additive (baseline) is the average of 14 wells tested with the diesel engine. In the period of measurement 1 the fuel additive has been applied for the first time to the diesel engine. Period of measurement 1 is followed by period of measurement 2, which in turn is followed by period of measurement 3. In the period of measurement 2 and 3 the same diesel engine has been used as for period of measurement 1.

In the following table 1 the fuel consumption is indicated as consumption of liters per hour (l/h) as average value for the respective day. FIG. 1 illustrates this result.

TABLE 1

Comparison of the reduction of fuel consumption without and with TBHP and TBA as fuel additive

| day | US base diesel fuel without TBHP in TBA (average consumption in l/h) | Period of measurement 1 US base diesel fuel with TBHP in TBA (average consumption in l/h) | Period of measurement 2 US base diesel fuel with TBHP in TBA (average consumption in l/h) | Period of measurement 3 US base diesel fuel with TBHP in TBA (average consumption in l/h) |
|---|---|---|---|---|
| 1 | 62.26 | 67.98 | 42.96 | 50 |
| 2 | 72.52 | 84.82 | 48.60 | 53.97 |
| 3 | 75.81 | 80.51 | 62.91 | 52.46 |
| 4 | 80.66 | 94.25 | 70.29 | 43.94 |
| 5 | 92.73 | 103.52 | 81.19 | 54.92 |
| 6 | 99.01 | 97.77 | 91.10 | 66.96 |
| 7 | 106.13 | 106.36 | 94.44 | 73.50 |
| 8 | 114.72 | 110.64 | 109.69 | 82.89 |
| 9 | 114.61 | 107.15 | 104.69 | 84.97 |
| 10 | 116.35 | 106.28 | 105.79 | 88.61 |
| 11 | 116.24 | 110.26 | 101.82 | 90.80 |
| 12 | 119.83 | 111.13 | 101.70 | 96.82 |
| 13 | 120.44 | 107.80 | 104.96 | 98.49 |
| 14 | 117.64 | 107.42 | 99.62 | 96.93 |
| 15 | 121.80 | 110.26 | 100.64 | 101.06 |
| 16 | 120.70 | 108.36 | 103.44 | 101.51 |
| 17 | 121.31 | 111.24 | 101.25 | 101.02 |
| 18 | 122.48 | 114.12 | 102.31 | 100.08 |
| 19 | 123.69 | 112.72 | 104.39 | 102.50 |
| 20 | 123.73 | 113.59 | 104.05 | 101.97 |
| 21 | 124.26 | 114.31 | 103.10 | 103.67 |
| 22 | 122.97 | 114.38 | 100.83 | 101.74 |
| average | 108.63 | 104.31 | 92.69 | 84.03 |

In the course of testing, an increase of fuel consumption was observed for fuel both with and without a fuel additive consisting of TBHP and TBA. Due to the use of the test engine in a drilling rig, the increase of fuel consumption depended on the earth drilled. With longer drilling periods, the drill advanced into deeper and more rigid layers of earth. In order to advance through more rigid layers of earth, the test engine needed more energy, hence consumed more fuel. Although the absolute values of fuel consumption are increasing during drilling, the relative values of fuel consumption of the fuel without and with fuel additive are decreasing.

Over the total period of measurement of 22 days an average consumption of 108.63 l/h was yielded for US base diesel fuel without fuel additive and of 104.31 l/h (period of measurement 1), 92.69 l/h (period of measurement 2) and 84.03 l/h (period of measurement 3) was yielded for the same US base diesel fuel with fuel additive. This corresponds to an average fuel saving of 4.32 l or 3.97% (period of measurement 1), 15.94 l or 14.67% (period of measurement 2) and 24.6 l or 22.65% (period of measurement 3) per hour measured.

It is observed that from day 1 to day 6 of period of measurement 1, the fuel consumption is higher using a fuel with fuel additive compared to a fuel without fuel additive. This is attributed to the cleaning of the engine by using the fuel with fuel additive. More fuel with fuel additive is consumed to reduce the deposits in the engine. From day 7 of period of measurement 1, the deposits in the engine are reduced to such an extend that lower fuel consumption compared to the baseline period is observed. During period of measurement 2 the engine is cleaned to such an extend that lower fuel consumption compared to period of measurement 1 is observed. During period of measurement 3 the engine is cleaned to such an extend that even lower fuel consumption compared to period of measurement 2 is observed.

This is also impressively demonstrated in a longer test over a period of 1306 hours 154662 l US base diesel fuel without fuel additive was consumed and 131684 l US base diesel fuel with fuel additive. This corresponds to a total fuel saving of 22978 l or 14.86%.

EXAMPLE 2

Reduction of Fuel Consumption with TBHP and TBA as Fuel Additive

To a US marine diesel (cetane number=40) was added 0.25 wt. % of a fuel additive consisting of TBHP (55 wt. %) and TBA (45 wt. %). The total amount of TBHP added to this diesel fuel is 0.14 wt. %.

The test engine used was a John Deere 6081 PowerTech 8.1 L, 6 cylinder, marine engine exhibiting a total displacement of 8100 cm$^3$, as well as a displacement per cylinder of 1350 cm$^3$ and a compression ratio of 15.7:1.

In a comparative test the consumption of the above mentioned US marine diesel was measured with and without diesel additive consisting of TBHP and TBA in the John Deere 6081 PowerTech 8.1 L marine diesel engine over a period of time of 25 days. The average consumption of diesel fuel without fuel additive was 25.55 l/h. The average consumption of the diesel fuel with diesel fuel additive was reduced compared to the diesel fuel without fuel additive during the period of measurement 1 (day 11-15) by 2.1%, during the period of measurement 2 (day 16-20) by 8.9% and during the period of measurement 3 (day 21-25) by 17.9%. This test result is illustrated in FIG. 2.

The increase of fuel consumption during day 1-5 and day 6-10 is due to removal of impurities and deposits in the engine which impurities clog the engine filter. Clogged filters have been changed on day 6, 11 and 16. From day 13 on, the engine is cleaned to such an extend that reduction in fuel consumption is observed.

EXAMPLE 3

Reduction of Fuel Consumption with TBHP and TBA as Fuel Additive

To a conventional US base diesel fuel (cetane number=42) was added 0.25 wt. % of a fuel additive consisting of TBHP (55 wt. %) and TBA (45 wt. %). The total amount of TBHP added to the diesel fuel is 0.14 wt. %.

In comparative tests the average consumption of the above mentioned base diesel fuel was measured without and with diesel fuel additive consisting of TBHP and TBA in diesel engines of various types of buses. In the following table 2 the average consumption is indicated as consumption in liters per 100 km for various buses.

TABLE 2

Comparison of the reduction of fuel consumption without and with TBHP and TBA as fuel additive in various types of buses.

| Bus No. | Bus description | US base diesel fuel without TBHP in TBA (average consumption in l/100 km) | US base diesel fuel with TBHP in TBA (average consumption in L/100 km) | total km travelled with a US base diesel fuel with TBHP in TBA | reduction of average consumption (in %) |
|---|---|---|---|---|---|
| 1 | 1995 Amtran International V 14.5 tons | 47.47 | 40.94 | 676 | 14 |
| 2 | 2002 Amtran International V 14.5 tons | 97.51 | 69.73 | 686 | 28 |
| 3 | 2008 Caterpillar I-6 16.5 tons | 47.00 | 41.37 | 3156 | 12 |
| 4 | 2008 Caterpillar I-6 16.5 tons | 44.17 | 40.80 | 3125 | 7.7 |
| 5 | 2008 Caterpillar I-6 16.5 tons | 43.20 | 39.76 | 3323 | 8.0 |
| 6 | 2008 Caterpillar I-6 16.5 tons | 44.59 | 40.24 | 2790 | 9.8 |
| 7 | 2008 Caterpillar I-6 16.5 tons | 44.51 | 39.97 | 2771 | 10 |
| 8 | 2008 Caterpillar I-6 16.5 tons | 40.73 | 28.21 | 3294 | 31 |
| 9 | 2008 Caterpillar I-6 16.5 tons | 46.35 | 27.04 | 3663 | 42 |
| 10 | 2009 Mercedes Benz I-6 16.5 tons | 38.59 | 35.77 | 2597 | 7.3 |
| 11 | 2009 Mercedes Benz I-6 16.5 tons | 40.73 | 37.72 | 2294 | 7.4 |

TABLE 2-continued

Comparison of the reduction of fuel consumption without and with TBHP and TBA as fuel additive in various types of buses.

| Bus No. | Bus description | US base diesel fuel without TBHP in TBA (average consumption in l/100 km) | US base diesel fuel with TBHP in TBA (average consumption in L/100 km) | total km travelled with a US base diesel fuel with TBHP in TBA | reduction of average consumption (in %) |
|---|---|---|---|---|---|
| 12 | 2009 Mercedes Benz I-6 16.5 tons | 47.19 | 42.41 | 3489 | 10 |
| 13 | 2009 Mercedes Benz I-6 16.5 tons | 46.53 | 28.38 | 2246 | 39 |

EXAMPLE 4

Reduction in Friction by Using TBHP and TBA as a Fuel Additive

To an untreated ultra-low sulfur diesel (cetane number=42) was added 0.25 wt. % of a fuel additive consisting of TBHP (55 wt. %) and TBA (45 wt. %). The total amount of TBHP added to the diesel fuel is 0.14 wt. %.

In comparative tests the HFRR score of the above mentioned untreated ultra-low sulfur diesel was measured without and with different diesel fuel additives. In the following table 3 the HFRR score of untreated ultra-low sulfur diesel is indicated as well as the HFRR score of ultra-low sulfur diesel with different fuel additives. Moreover, the HFRR score of the fuel with fuel additive is compared to the fuel without fuel additive.

TABLE 3

HFRR score of base fuel without as well as with diesel additives

| | Additive/Fuel | HFRR score | Reduction |
|---|---|---|---|
| | Standard Engine Manufacturers Association (desired) | <460 | |
| | Untreated ultra-low sulfur diesel | 636 | |
| 1 | 2-EHN (25.3-38.6 wt. %); petroleum naphta (27.2-41.3 wt. %) trimethyl-benzene (0.4-1.96 wt. %), naphthalene (3.12 wt. %), 2-ethylhexanol (0.4-1.96 wt. %) | 447 | 189 |
| 2 | 2-EHN (10-19.9 wt. %), petroleum naphta (60-69 wt. %) trimethylbenzene (20-29 wt %) | 461 | 175 |
| 3 | 2-EHN (30-60 wt. %), light aromatic petroleum naphta (30-60 wt. %) 1,2,4-trimethylbenzene (10-30 wt. %) | 470 | 166 |
| 4 | 1,2,4-trimethylbenzene (30-60 wt. %) trimethylbenzene (30-60 wt. %) solvent naphta, heavy aromatic (5-10 wt. %) | 488 | 148 |
| 5 | Distillates petroleum, hydrotreated light (30-50 wt. %), 2-EHN (20-30 wt. %), naphta (petroleum), heavy aromatic 10-30 wt. %) | 603 | 33 |
| 6 | TBHP (55 wt. %), TBA (45 wt. %) | 316 | 320 |

The diesel additive consisting of TBHP and TBA resulted in a reduction of the HFRR score of 320 and is below the standard of the Engine Manufacturers Association.

EXAMPLE 5

Reduction of Fuel Consumption with DTBP, CH or TBHP as Fuel Additive

Tests were performed, wherein to a conventional diesel fuel (cetane number=42) was added each 0.25 wt. % of a fuel additive comprising DTBP, CH or TBHP, respectively, whereby in each of the used fuel additive formulations DTBP was present in pure form, CH as a 80% solution in isododecane and TBHP as a 55% solution in TBA. The total amount of DTBP added to the diesel fuel is 0.25 wt. %. The total amount of CH added to the diesel fuel is 0.20 wt. %. The total amount of TBHP added to the diesel fuel is 0.14 wt %.

The diesel generator used in each of the tests was a SDMO 30 kVA generator with a 2.9l 3-cylinder diesel John Deere motor. The diesel fuel used for testing was Engen Dynamic Diesel 50 ppm. The test engine was used at a temperature range between 25° C. to 31° C.

In a comparative test, the consumption of the above-mentioned diesel fuel was measured without and with diesel fuel additive consisting of DTBP, CH or TBHP. The measurement of fuel consumption (under no load condition) of the US based diesel fuel without diesel fuel additive (base line) was established over a course of seven individual 30-minute runs using 2l of untreated fuel. For testing the fuel additives, the generator fuel system was purged with 2 l of fuel treated with the respective fuel additives and the diesel consumption (under no load condition) using the treated fuel was established over a course of seven individual 30-minute runs.

In the following Table 4, the full consumption is indicated as consumption of milliliter as average value for the respective run.

TABLE 4

| Run (30 minutes) | Pure 50 ppm Diesel | DTBP dosed diesel | CH dosed diesel | TBHP dosed diesel |
|---|---|---|---|---|
| 1 | 735 | 630 | 660 | 660 |
| 2 | 780 | 672 | 648 | 639 |
| 3 | 690 | 690 | 645 | 639 |
| 4 | 690 | 711 | 630 | 666 |
| 5 | 723 | 660 | 645 | 669 |
| 6 | 744 | 666 | 639 | 651 |
| 7 | 729 | 687 | 645 | 624 |
| Average consumption per run (ml) | 727.29 | 673.71 | 644.57 | 649.71 |
| Average consumption per hour (ml) | 1454.57 | 1347.43 | 1289.14 | 1299.43 |
| Average diesel consumption reduction (ml) | | 53.57 | 82.71 | 77.57 |
| Percentage reduction | | 7.37% | 11.37% | 10.67% |

Over the total period of measurement of seven runs, an average consumption per run of 727.29 ml/run was yielded for the diesel fuel without fuel additive. A reduction of average fuel consumption to 673.71 ml/run (DTBP), 644.75 ml/run (CH) and 649.71 ml/run (TBHP) was yielded for the diesel fuel dosed with the respective fuel additives. This corresponds to an average reduction of fuel consumption of 53.57 ml/run and percentage reduction of 7.37% for DTBP dosed fuel additive, and respectively of 82.71 ml/run and 11.37% for CH dosed fuel additive and 77.57 ml/run and 10.67% for TBHP fuel additive for the overall measurement.

These test results indicate that each of the three fuel additives have a significant and immediate impact of reducing diesel consumption when added to a US base diesel fuel.

Moreover, a marked and immediate visual impact of reduced smoke emission and cleaner (whiter) smoke emission could be observed (data not shown) from the generator when using the diesel treated with the fuel additives as opposed to the untreated diesel.

The invention claimed is:

1. A method for preventing, reducing and/or removing deposits in a diesel engine comprising:
   adding a fuel additive comprising a peroxide to a diesel fuel; and,
   permitting a diesel engine to combust the fuel additive and the diesel fuel,
      wherein the fuel additive prevents, reduces and/or removes deposits formed in the diesel engine during the combustion.

2. The method of claim 1, wherein the fuel additive comprises at least one organic peroxide.

3. The method of claim 2, wherein the at least one organic peroxide is a hydroperoxide, dialkylperoxide, a cyclic or acyclic ketone peroxide, a perketal or a combination thereof.

4. The method of claim 1, wherein the fuel additive comprises tert-butylhydroperoxide (TBHP), cumene hydroperoxide, methylethylketoneperoxide, acetone peroxide, tert-amyl hydroperoxide (TAHP), di-tert-butyl peroxide (DTBP), tert-butyl peroxybenzoate (TBPB), 1,1-Di-(tert-butylperoxy)-cyclohexan (CH) or tetramethyl-dioxa-cyclohexane (TMDOCH).

5. The method of claim 1, wherein the fuel additive comprises TBHP.

6. The method of claim 1, wherein the fuel additive comprises DTBP.

7. The method of claim 1, wherein the fuel additive comprises CH.

8. The method of claim 1, wherein the fuel additive is anhydrous.

9. The method of claim 8, wherein water in the anhydrous fuel additive is <5 wt.

10. The method of claim 1, wherein the fuel additive further comprises a solvent, wherein the solvent is an alcohol or a hydrocarbon.

11. The method of claim 10, wherein the alcohol is tert-butyl alcohol, and the hydrocarbon is isododecane, diesel, kerosene or 2,2,4-trimethyl-1,3-pentanediol diisobutyrate.

12. The method of claim 1, wherein the fuel additive comprises a mixture of TBHP and tert-butyl alcohol (TBA).

13. The method of claim 12, wherein the TBHP is anhydrous TBHP.

14. The method of claim 1, wherein the peroxide is in an amount of 0.001 wt. % to 10 wt. based on the total weight of the fuel.

15. The method of claim 1, wherein the deposits comprise small particles, soot and/or glycol.

16. The method of claim 1, wherein the diesel fuel with the fuel additive has a HFRR score of at least 70 lower than the diesel fuel without the fuel additive.

17. The method of claim 1, wherein the diesel fuel without the fuel additive has a cetane number of <50.

18. The method of claim 1, wherein the diesel fuel with fuel additive has a cetane number larger by at least 2 compared to the diesel fuel without fuel additive.

19. The method of claim 8, wherein water in the anhydrous fuel additive is <1 wt. %.

20. The method of claim 8, wherein water in the anhydrous fuel additive is <0.3 wt. %.

21. The method of claim 8, wherein water in the anhydrous fuel additive is <0.01 wt. %.

22. The method of claim 1, wherein the peroxide is in an amount of 0.25 wt. % to 10 wt. % based on the total weight of the fuel.

23. The method of claim 1, wherein the peroxide is in an amount of 0.1 wt. % to 3 wt. % based on the total weight of the fuel.

24. The method of claim 1, wherein the peroxide is in an amount of 0.1 to 0.5 wt. % based on the total weight of the fuel.

25. The method of claim 1, wherein the diesel fuel without the fuel additive has a cetane number of <45.

* * * * *